(12) United States Patent  (10) Patent No.: US 7,374,420 B2
Brennan et al.  (45) Date of Patent: *May 20, 2008

(54) MULTI-LAYER ADHESIVES AND METHODS FOR BONDING ORTHODONTIC APPLIANCES TO TOOTH STRUCTURE

(75) Inventors: Joan V. Brennan, Sierra Madre, CA (US); David K. Cinader, Yorba Linda, CA (US); James D. Hansen, Woodbury, MN (US); Darrell S. James, Covina, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 518 days.

This patent is subject to a terminal disclaimer.

(21) Appl. No.: 10/740,980

(22) Filed: Dec. 19, 2003

(65) Prior Publication Data

US 2005/0136370 A1  Jun. 23, 2005

(51) Int. Cl.
*A61C 3/00* (2006.01)
(52) U.S. Cl. .................................................. 433/9
(58) Field of Classification Search .............. 433/8, 433/9, 17
See application file for complete search history.

(56) References Cited

U.S. PATENT DOCUMENTS

| | | | |
|---|---|---|---|
| 3,797,115 A | 3/1974 | Silverman et al. | |
| 3,814,717 A | 6/1974 | Wilson et al. | |
| 4,204,325 A | 5/1980 | Kaelble | |
| 4,340,529 A * | 7/1982 | Lee et al. | 524/105 |
| 4,948,366 A * | 8/1990 | Horn et al. | 433/9 |
| 4,948,367 A | 8/1990 | Haas | |
| 4,978,007 A | 12/1990 | Jacobs et al. | |
| 5,015,180 A | 5/1991 | Randklev | |
| 5,172,809 A * | 12/1992 | Jacobs et al. | 206/368 |
| 5,183,403 A | 2/1993 | Masuhara et al. | |
| 5,219,283 A * | 6/1993 | Farzin-Nia et al. | 433/9 |
| 5,221,202 A | 6/1993 | James | |
| 5,269,680 A * | 12/1993 | Kawaguchi | 433/9 |
| 5,295,824 A | 3/1994 | Wong | |
| 5,328,363 A | 7/1994 | Chester et al. | |
| 5,348,154 A | 9/1994 | Jacobs et al. | |
| 5,350,059 A | 9/1994 | Chester et al. | |
| 5,354,199 A | 10/1994 | Jacobs et al. | |
| 5,429,229 A | 7/1995 | Chester et al. | |
| 5,538,129 A | 7/1996 | Chester et al. | |
| 5,552,177 A | 9/1996 | Jacobs et al. | |

(Continued)

FOREIGN PATENT DOCUMENTS

WO   WO 00/69393   11/2000

OTHER PUBLICATIONS

Product Information Brochure Specifications: Automotive® A-400 Series, Automated Fluid Dispensing Systems, Asymtek® A Nordson Company, 2 pgs. (Aug. 2000).

*Primary Examiner*—Ralph A. Lewis
(74) *Attorney, Agent, or Firm*—James D. Christoff

(57) ABSTRACT

The present invention provides multi-layer adhesives and methods that are useful for bonding orthodontic appliances to a tooth structure. The multi-layer adhesives can be precoated on an orthodontic appliance, or alternatively, they can be provided on an adhesive delivery system for transfer to an orthodontic appliance. The multi-layer adhesives and methods preferably provide a useful balance of properties for bonding orthodontic appliances to the tooth structure.

38 Claims, 3 Drawing Sheets

U.S. PATENT DOCUMENTS

| | | |
|---|---|---|
| 5,558,516 A | 9/1996 | Horn et al. |
| 5,575,645 A | 11/1996 | Jacobs et al. |
| 5,636,736 A | 6/1997 | Jacobs et al. |
| 5,746,594 A | 5/1998 | Jordan et al. |
| 5,762,192 A | 6/1998 | Jacobs et al. |
| 5,810,584 A | 9/1998 | Wong |
| 5,827,058 A | 10/1998 | Kelly et al. |
| 5,897,312 A * | 4/1999 | Chikami ........................ 433/9 |
| 5,971,754 A | 10/1999 | Sondhi et al. |
| 6,050,815 A | 4/2000 | Adam et al. |
| 6,089,861 A * | 7/2000 | Kelly et al. .................... 433/9 |
| 6,089,868 A | 7/2000 | Jordan et al. |
| 6,126,922 A | 10/2000 | Rozzi et al. |
| 6,183,249 B1 * | 2/2001 | Brennan et al. ................ 433/9 |
| 6,213,767 B1 * | 4/2001 | Dixon et al. .................... 433/9 |
| 6,331,080 B1 | 12/2001 | Cole et al. |
| 6,350,119 B1 | 2/2002 | Jordan et al. |
| 6,444,725 B1 | 9/2002 | Trom et al. |
| 6,513,897 B2 | 2/2003 | Tokie |
| 6,528,555 B1 * | 3/2003 | Nikutowski et al. ........ 523/116 |
| 6,746,242 B1 * | 6/2004 | Kesling ......................... 433/9 |
| 7,137,812 B2 * | 11/2006 | Cleary et al. .................. 433/3 |
| 2002/0173770 A1 * | 11/2002 | Flory et al. .................. 604/537 |
| 2003/0196914 A1 | 10/2003 | Tzou et al. |
| 2003/0198914 A1 | 10/2003 | Brennan et al. |

* cited by examiner

MULTI-LAYER ADHESIVES AND METHODS FOR BONDING ORTHODONTIC APPLIANCES TO TOOTH STRUCTURE

BACKGROUND

Orthodontic treatment involves movement of malpositioned teeth to orthodontically correct positions. Tiny orthodontic appliances known as brackets are connected to exterior surfaces of the patient's teeth, and an archwire is placed in a slot of each bracket. The archwire forms a track to guide movement of the teeth to desired positions for correct occlusion. End sections of the archwire are often received in appliances known as buccal tubes that are fixed to the patient's molar teeth. In recent years it has become common practice to use adhesives to bond orthodontic appliances to the surface of the tooth, using either direct or indirect methods.

For many years, it was common practice to apply orthodontic adhesive to the base of the appliance immediately before the appliance was placed on the tooth. In some instances, a quantity of adhesive was dispensed onto a mixing pad or dispensing well, and a small spatula or other hand instrument was then used to apply a small dab of adhesive to each appliance. In other instances, a quantity of adhesive was dispensed from a syringe directly onto the base of the appliance.

Adhesive precoated brackets are known and offer significant advantages to the orthodontist. Adhesive precoated brackets have a bonding base upon which the manufacturer may apply a precise quantity of adhesive such as a photocurable adhesive. In direct bonding methods, when it is desired to mount the bracket on a tooth, the bracket is simply removed from the package and placed directly onto the tooth. For indirect bonding methods, brackets are removed from the package and placed, for example, on a replica plaster or "stone" model of the patient's dental arch to provide a custom base for later mounting on the patient's tooth, commonly using a transfer tray.

In addition to good handling properties and adequate adhesion, practitioners often desire that photocurable adhesives provide other desirable functional properties, including, for example, sustained fluoride release. In many applications, it is also desirable that the adhesive have adequate hydrophilicity or moisture tolerance, as indicated, for example, by the ability of the adhesive to absorb water or saliva, and/or the ability to provide an adequate bond under moist conditions.

Orthodontic brackets precoated with an adhesive are commonly sold with a flexible release substrate in contact with the adhesive. However, many release substrates are not suitable for use with all adhesives. For example, when soft, tacky, less viscous, hydrophilic adhesives are used, it has been found that a portion of the adhesive is sometimes left on the release substrate when an attempt is made to lift the appliance from the container and detach the adhesive from the release substrate. In those instances, sufficient adhesive may not remain on the bracket to provide adequate bond strength to retain the bracket on the tooth during the course of orthodontic treatment. Moreover, adhesives having a relatively low viscosity tend to slowly flow across the release substrate and from the space beneath the bracket over extended periods of time, creating bracket removal and/or liner release problems.

Additionally, when soft, tacky, less viscous adhesives are used with conventional adhesive precoated appliance packages, the shape of the adhesive may distort as the appliance is lifted from the container. In some instances, detaching the adhesive from the release substrate may alter the configuration of the adhesive, resulting in unsatisfactory direct bonding unless additional steps are undertaken to shift the adhesive by hand back to its original, pillow-like shape. For example, when lifting an appliance from the container, some of the adhesive may be shifted to one side of the appliance base, such that the opposite side of the base does not have a satisfactory amount of adhesive for bonding. If the appliance is secured to a tooth structure in such a manner that a void space is present between a portion of the base and the opposed tooth surface, the void space may result in premature, spontaneous debonding of the appliance from the tooth, a nuisance that is best avoided. Furthermore, in some instances the void space can establish a pocket that receives food and debris, facilitating the formation of caries.

Presently, there is a need in the art for adhesives and methods that provide a balance of properties and characteristics that are desired by the practitioner.

SUMMARY OF THE INVENTION

In one aspect, the present invention provides a packaged article. The packaged article includes: an orthodontic appliance having a base for bonding the appliance to a tooth structure; a first hardenable adhesive layer and a second hardenable adhesive layer, each extending across at least a portion of the base of the appliance; and a container at least partially surrounding the orthodontic appliance having the first and second layers thereon. Each of the adhesive layers may independently be patterned or non-patterned. Each of the adhesive layers may independently include, for example, light cure or chemical cure adhesives. Optionally, one or more additional hardenable adhesive layers, which may be in contact with a release substrate, extend across at least a portion of the first or second layers. In one embodiment, the first and second layers are not in contact with a release substrate. In another embodiment, the appliance is suspended in the package.

In another aspect, the present invention provides an article including: an orthodontic appliance having a base for bonding the appliance to a tooth structure; and a first hardenable adhesive layer and a second hardenable adhesive layer, each extending across at least a portion of the base of the appliance, wherein at least one of the first or second adhesive layers includes a photobleachable dye, and wherein the at least one adhesive has an initial color prior to exposure to actinic radiation and a final color subsequent to exposure to actinic radiation, the initial color being different than the final color. Optionally, one or more additional hardenable adhesive layers extend across at least a portion of the first or second layers. Preferably, at least one of the first or second layers further includes a hardener including a sensitizing compound different from the photobleachable dye.

In another aspect, the present invention provides an article including: an orthodontic appliance having a base for bonding the appliance to a tooth structure; a first hardenable adhesive layer extending across at least a portion of the base of the appliance and covering a first area; and a second hardenable adhesive layer extending across at least a portion of the base of the appliance and covering a second area, wherein the second area is different than the first area. In some embodiments, the first area is coextensive with the base of the appliance. In some embodiments, the second area is smaller than the first area. In some embodiments, one of the areas is proximate the center of the base of the appliance. In some embodiments, one of the areas is proximate the periphery of the base of the appliance. Optionally, one or more additional hardenable adhesive layers extend across at least a portion of the first or second layers.

In another aspect, the present invention provides an orthodontic adhesive delivery system or a packaged orthodontic adhesive delivery system. The system includes: a substrate including an adhesive transfer area; a first hardenable adhesive layer extending across at least a portion of the adhesive transfer area; and a second hardenable adhesive layer extending across at least a portion of the first hardenable adhesive layer. In some embodiments, at least one of the first or second layers is in the form of dots or lines. Optionally, one or more additional hardenable adhesive layers extend across at least a portion of the first or second hardenable adhesive layer.

In another aspect, the present invention provides an orthodontic adhesive delivery or a packaged orthodontic adhesive delivery system. The system includes: a substrate including an adhesive transfer area; and a first hardenable adhesive layer and a second hardenable adhesive layer, each extending across at least a portion of the adhesive transfer area, with the proviso that the first and second hardenable layers are not different parts of a multi-part, chemical cure adhesive.

The present invention also provides methods of making and using precoated orthodontic devices and orthodontic adhesive delivery systems.

Definitions

As used herein, "orthodontic appliance" refers to any device intended to be bonded to a tooth structure, including, but not limited to, orthodontic brackets, buccal tubes, bite openers, buttons, and cleats. Thus, the term "orthodontic appliance" encompasses orthodontic bands. The appliance has a base for receiving adhesive and it can be a flange made of metal, plastic, ceramic, and combinations thereof. Alternatively, the base can be a custom base formed from cured adhesive layer(s) (i.e., single or multi-layer adhesives).

As used herein, a "packaged" article refers to an orthodontic appliance or card that is received in a container. Preferably, the container provides protection from environmental conditions including, for example, moisture and light.

As used herein, a "release" substrate refers to a substrate in contact with an article that is removed from the article before or during use of the article.

As used herein, a "multi-layer" adhesive refers to an adhesive having two or more layers.

As used herein, a "layer" refers to a discontinuous (e.g., a patterned layer) or continuous (e.g., non-patterned) material extending across all or a portion of a different material. A layer may be of uniform or varying thickness.

As used herein, a "patterned layer" refers to a discontinuous layer in which the material of the patterned layer extends across only selected portions of another material.

As used herein, a "non-patterned layer" refers to a continuous layer in which the material of the non-patterned layer extends across an entire portion of another material.

In general, a layer "extending across" or "attached to" another layer is intended to be broadly interpreted to optionally include one or more additional layers between the two layers.

As used herein, "hardenable" is descriptive of a material that can be cured or solidified, for example, by heating to remove solvent, heating to cause polymerization, chemical cross-linking, radiation-induced polymerization, or crosslinking.

As used herein, "hardener" means a system that initiates hardening of a resin. A hardener may include, for example, a polymerization initiator.

As used herein, "photobleachable" refers to loss of color upon exposure to actinic radiation.

As used herein, "filler" means a particulate material (e.g., an inorganic oxide) in dry powder form capable of being dispersed in a resin. For example, a dental composite preferably includes a powder dispersed in a resin.

As used herein, the term "(meth)acrylate" is a shorthand reference to acrylate, methacrylate, or combinations thereof, and "(meth)acrylic" is a shorthand reference to acrylic, methacrylic, or combinations thereof.

As used herein, the chemical term "group" allows for substitution.

As used herein, "a" or "an" means one or more.

DETAILED DESCRIPTION OF PREFERRED EMBODIMENTS

The present invention provides multi-layer adhesives (i.e., two or more hardenable adhesive layers) and methods using the multi-layer adhesives for bonding orthodontic appliances to a tooth structure. In some embodiments, the multi-layer adhesives are provided precoated on an orthodontic appliance. In other embodiments, the multi-layer adhesives are provided on an orthodontic adhesive delivery system, and are subsequently transferred to an orthodontic appliance. The multi-layer adhesives are preferably provided as packaged articles, with or without release substrates, such as those described, for example, in U.S. Pat. No. 6,183,249 (Brennan et al.).

Figure 1:
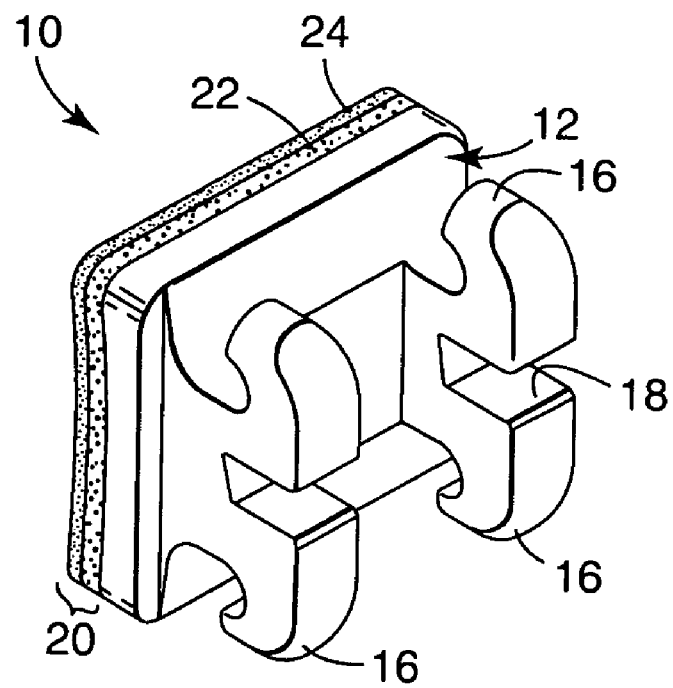
FIG. 1 is perspective view of an orthodontic appliance having a multi-layer adhesive on the base thereof.
Figure 2:
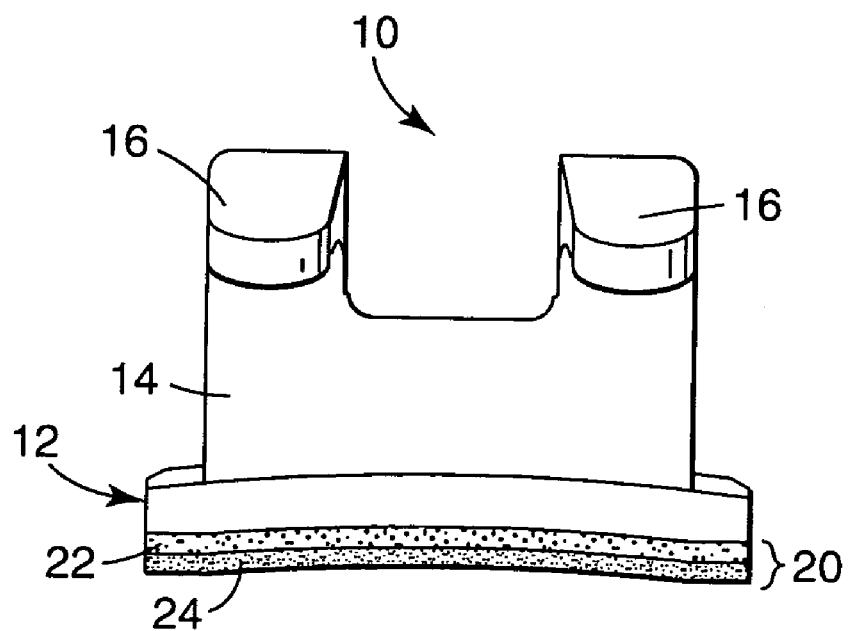
FIG. 2 is a side view of the orthodontic appliance of FIG. 1.

In FIGS. 1 and 2, an exemplary orthodontic appliance is designated by the numeral 10 and is a bracket, although other appliances such as buccal tubes, buttons and other attachments are also possible. The appliance 10 includes a base 12. The appliance 10 also has a body 14 that extends outwardly from the base 12. Base 12 can be a flange made of metal, plastic, ceramic, and combinations thereof. Alternatively, the base 12 can be a custom base formed from cured adhesive layer(s) (i.e., single or multi-layer adhesives). Tiewings 16 are connected to the body 14, and an archwire slot 18 extends through a space between the tiewings 16. The base 12, the body 14, and tiewings 16 may be made of any one of a number of materials suitable for use in the oral cavity and having sufficient strength to withstand the correction forces applied during treatment. Suitable materials include, for example, metallic materials (such as stainless steel), ceramic materials (such as monocrystalline or polycrystalline alumina), and plastic materials (such as fiber-reinforced polycarbonate). Optionally, the base 12, the body 14, and the tiewings 16 are integrally made as a unitary component.

A multi-layer adhesive 20 extends across the base 12 of the appliance 10. The multi-layer adhesive 20 serves in whole or at least in part to securely fix the appliance 10 to the patient's tooth by a bond having sufficient strength to resist unintended detachment from the tooth during the course of treatment. Preferably, the multi-layer adhesive 20 is applied by the manufacturer to the base 12 of the appliance 10.

The multi-layer adhesive 20 illustrated in FIGS. 1 and 2 includes adhesive layer 22 extending across base 12, and adhesive layer 24 extending across base 12 and adhesive layer 22. It should be understood that multi-layer adhesive 20 can include additional layers that are not illustrated in FIGS. 1 and 2. Layers 22 and 24 are layers of different adhesives that may or may not cover the same area. Layers 22 and 24 may independently be discontinuous (e.g., a patterned layer) or continuous (e.g., non-patterned) material extending across all or a portion of another material.

Adhesive layers 22 and 24 may differ in properties including, for example, chemical composition; viscosity; hydrophilicity as disclosed, for example, in U.S. Pat. No. 6,126,922 (Rozzi et al.); thickness; curing times; curing mechanisms; color; change in color upon curing; enzyme release; fluoride release; bond strengths upon curing; filler loading; filler types; and pH (as disclosed, for example, in PCT International Publication No. WO 00/69393 (Brennan et al.).

Adhesive layers 22 and 24 may each be a liquid, a paste, or a solid material that is converted into a liquid or paste during the bonding procedure. Suitable compositions include composites, compomers, glass ionomers and resin-modified glass ionomers. Examples of light-curable adhesives include Transbond XT brand and Transbond LR brand adhesives from 3M Unitek. Examples of chemical curing adhesives include Sondhi brand Rapid-Set indirect bonding adhesive, Unite brand adhesive, Concise brand adhesive and Multi-Cure brand glass ionomer cement from 3M Unitek.

Compositions useful in adhesive layers of the present invention are well known to one of skill in the art. Useful compositions include, for example, both light cure and chemical cure orthodontic adhesives. In some embodiments, the compositions are preferably fluoride releasing adhesives, self etching adhesives, self priming adhesives, color-changing adhesives, and combinations thereof.

Optionally, the composition is an adhesive that falls in one of the following classes in accordance with the practitioner's preferences for tooth treatment:

Class I: An adhesive that requires both etching of tooth enamel (using, for example, phosphoric acid or a bisphosphonic acid) and a separate application of a primer to the tooth enamel.

Class II: An adhesive that requires etching (using, for example, phosphoric acid, a bisphosphonic acid or self-etching primer) but not a separate application of primer.

Class III: An adhesive that requires no treatment of the teeth other than cleaning.

Possible primers for use with class I adhesives include orthodontic primers such as Transbond MIP brand primer and Transbond XT brand primer from 3M Unitek and Ortho Solo brand primer from Ormco Corporation. Optionally, the primer may include a photobleachable dye to ensure adequate coverage of the primer on the teeth, a small amount of fluoroalumina silicate glass ("FAS" glass) for providing fluoride release during treatment, a small amount of fumed silica for rheology control purposes, and/or a small amount of silanated quartz filler for enhanced fracture toughness.

Suitable class II adhesives include the adhesives mentioned above. The layer first contacting the tooth can be replaced by a self-etching primer such as Transbond Plus SEP brand primer from 3M Unitek. Optionally, the self-etching primer could incorporate the optional features described above for the class I adhesive.

Suitable class III adhesives avoid the need for etching and priming the teeth and may be referred to as "self-adhesive" compositions. With these adhesives, the practitioner need only clean the teeth prior to application of the dental appliance in a typical bonding procedure. Suitable class III adhesives may include an acid component selected from a methacrylate phosphate (e.g., mono-HEMA phosphate, di-HEMA phosphate, glycerol dimethacrylate (GDMA) phosphate), a solution of a bisphosphonic acid in water or other solvent, and a bisphosphonic acid in powder form (using water for ionizing that is left on the teeth after tooth prophy and rinse). Other class III adhesives may include an ethylenically unsaturated component with acid functionality, an ethylenically unsaturated component without acid functionality, an initiator system, and a filler. Optionally a class III adhesive may be essentially free of water. Examples of class III adhesives have been previously described, e.g. in pending U.S. Provisional Pat. Application No. 60/494,603 filed Aug. 12, 2003.

The class III adhesives described above can optionally incorporate fillers (e.g., a glass ionomer-type filler that binds the water in the usual glass ionomer setting reaction). In addition, any of the class III adhesives described above may incorporate the optional features described in connection with class I adhesives.

Adhesives useful in the present invention may optionally include components such as fluoride releasing agents as described, for example, in U.S. Pat. No. 3,814,717 (Wilson et al.) and U.S. Pat. No. 6,126,922 (Rozzi et al.); adhesive enhancing agents (e.g., titanites, zirconates) as disclosed, for example, in PCT International Publication No. WO 00/69393 (Brennan et al.); fillers; micro fillers; enzyme releasing agents; rheology enhancing agents; photobleachable dyes; and combinations thereof.

In some embodiments, one or more adhesives in multi-layer adhesives of the present invention preferably have an initial color remarkably different than dental structures. Color is preferably imparted to the composition through the use of a photobleachable dye. The composition preferably includes at least 0.001% by weight photobleachable dye, and more preferably at least 0.002% by weight photobleachable dye, based on the total weight of the composition. The composition preferably includes at most 1% by weight photobleachable dye, and more preferably at most 0.1% by weight photobleachable dye, based on the total weight of the composition. The amount of photobleachable dye may vary depending on its extinction coefficient, the ability of the human eye to discern the initial color, and the desired color change.

The color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the composition and evaluating the change in color. Preferably, at least one photobleachable dye is at least partially soluble in a hardenable resin.

Exemplary classes of photobleachable dyes are disclosed, for example, in U.S. Pat. No. 6,331,080 (Cole et al.), U.S. Pat. No. 6,444,725 (Trom et al.), and 6,528,555 (Nikutowski et al.). Preferred dyes include, for example, Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof.

The color change in the adhesives is initiated by light. Preferably, the composition's color change is initiated using actinic radiation using, for example, a dental curing light which emits visible or near infrared (IR) light for a sufficient amount of time. The mechanism that initiates the color change in the compositions of the invention may be separate from or substantially simultaneous with the hardening mechanism that hardens the resin. For example, a composition may harden when polymerization is initiated chemically (e.g., redox initiation) or thermally, and the color change from an initial color to a final color may occur subsequent to the hardening process upon exposure to actinic radiation.

The change in composition color from an initial color to a final color is preferably quantified by a Color Test as described below. Using the Color Test, a value of $\Delta E^*$ is determined, which indicates the total color change in a 3-dimensional color space. The human eye can detect a color change of approximately 3 $\Delta E^*$ units in normal lighting conditions. The dental compositions of the present invention are preferably capable of having a color change, $\Delta E^*$, of at least 10; more preferably, $\Delta E^*$ is at least 15; most preferably $\Delta E^*$ is at least 20.

Each layer of the multi-layer adhesive can be patterned or non-patterned. The layers can cover the same or different areas of the appliance or adhesive delivery system. One layer can cover none of, partially cover, or fully cover another adhesive layer. Patterned layers may be in forms including, for example, lines, dots, squares, circles, and combinations thereof. Layers can be of uniform or varying thickness.

FIGS. 3-6 are bottom views of exemplary embodiments of articles 30 (e.g., orthodontic appliances or adhesive delivery systems) having multi-layer adhesives 32 thereon. If article 30 is an orthodontic appliance, then numeral 32 represents the base of the appliance. Base 32 can be a flange made of metal, plastic, ceramic, and combinations thereof. Alternatively, base 32 can be a custom base formed from cured adhesive layer(s) (i.e., single or multi-layer adhesives). If article 30 is an adhesive delivery system, then numeral 32 represents the adhesive transfer area of a substrate.

Figure 3:
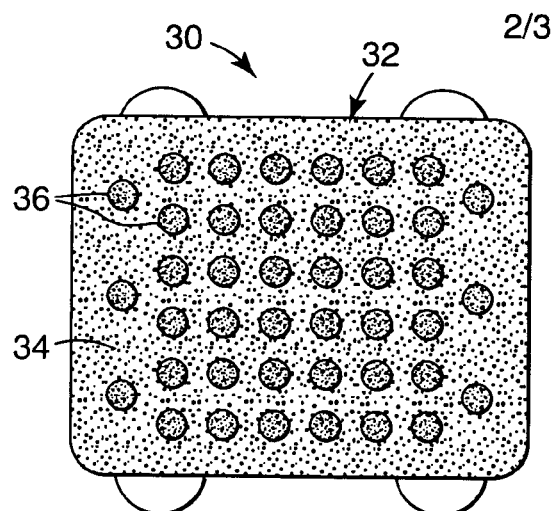
FIGS. 3-6 are bottom views of exemplary embodiments of articles (e.g., orthodontic appliances or adhesive delivery systems) having multi-layer adhesives thereon.
Figure 4:
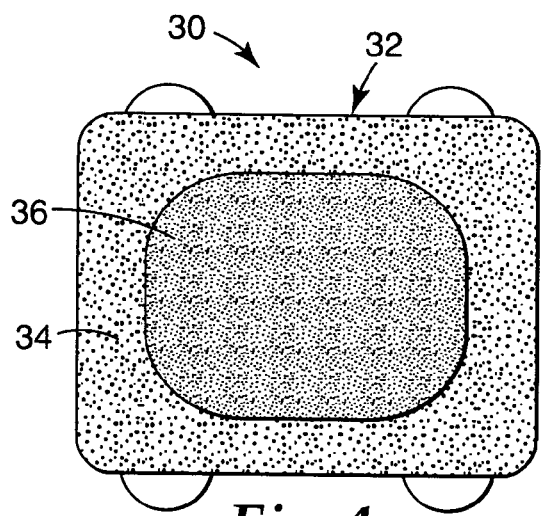
Figure 5:
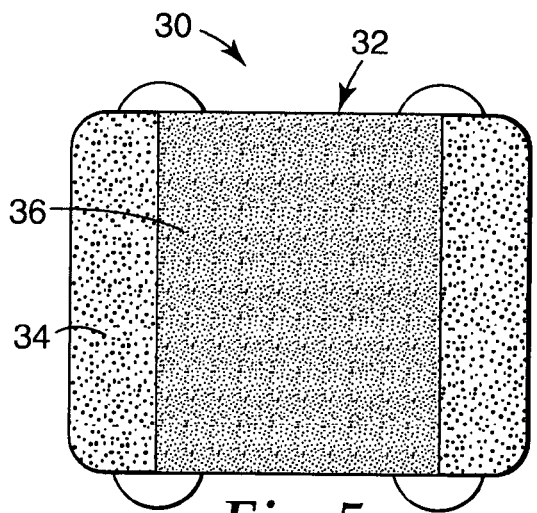

Referring to FIGS. 3-5, in some embodiments, adhesive layer 34 may represent a continuous layer that is coextensive with the area of the base or adhesive transfer area 32. Alternatively, in some embodiments, adhesive layer 34 may represent a discontinuous layer that covers only the lighter stipled area.

In the exemplary embodiments illustrated in FIGS. 3-5, adhesive layer 36 represents a discontinuous layer extending across only the portions of the base or adhesive transfer area 32 indicated by the darker stipled areas. Referring to FIG. 3, discontinuous adhesive layer 36 is a patterned layer represented as a pattern of darker stipled dots. Referring to FIG. 4, discontinuous adhesive layer 36 is represented as the single darker stipled "donut hole" area. Referring to FIG. 5, discontinuous adhesive layer 36 is represented as the single darker stipled square area.

In embodiments where adhesive layer 34 represents a continuous layer, adhesive layer 36 extends across the portions of layer 34 indicated by the darker stipled areas. Alternatively, in embodiments where adhesive layer 34 represents a discontinuous layer that covers only the lighter stipled areas, adhesive layer 36 may extend across the portions of base or adhesive transfer area 32 indicated by the darker stipled areas.

Figure 6:
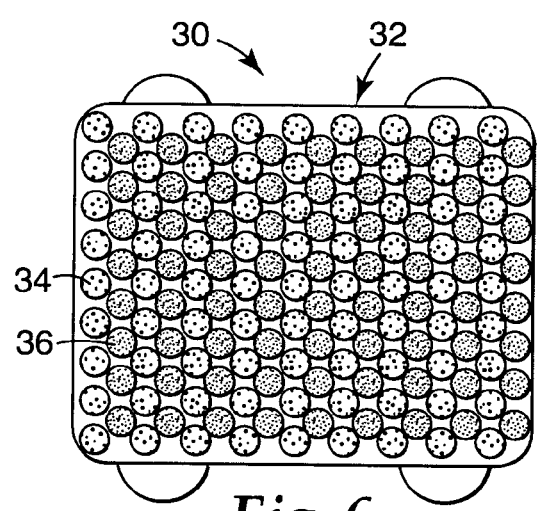

In the exemplary embodiment illustrated in FIG. 6, adhesive layers 34 and 36 are both discontinuous layers. Adhesive layer 34 extends across the portions of base or adhesive transfer area 32 indicated by the lighter stipled areas as a pattern of dots. Similarly, adhesive layer 36 extends across the portions of base or adhesive transfer area 32 indicated by the darker stipled areas as a pattern of dots. In the embodiment illustrated in FIG. 6, none of the dots of adhesive layer 36 extend across adhesive layer 34. However, in other embodiments (not illustrated), dots or portions of dots of adhesive layer 36 can extend across adhesive layer 34. Alternatively, both of dots 34 and 36 could be located on base or adhesive transfer area 32 and contact each other. When article 30 is an adhesive delivery system and numeral 32 represents the adhesive transfer area of a substrate, then either (i) adhesive layers 34 and 36 are not different parts of a multi-part, chemical cure adhesive, or (ii) another layer (not illustrated) extends across at least a portion of adhesive layer 34 or 36.

In some embodiments, the multi-layer adhesives and methods described herein offer advantages over adhesives known in the art. Benefits preferably include increased bonding efficiency and/or a decreased number of bonding steps. Preferably, the bond strength is increased, thereby reducing the incidence of bond failures. For example, a first layer may be selected for properties specific to the bracket being used (e.g., size and construction of the base), a second layer may be selected to provide the desired bond strength for the specific application (posterior or cuspid/bicuspid applications), and a third layer may be selected to conform with the specific tooth surface to which the bracket will be attached.

In some embodiments, the orthodontic appliances described herein may be used without priming the tooth, thereby decreasing the number of steps required in the bonding procedure and saving both the clinician and the patient time and money. Other advantages include, for example, the opportunity to tailor overall adhesive properties by using a combination of adhesives with different properties in the multi-layer construction.

In some embodiments, the adhesive layers can be patterned to provide for desired properties including, for example, easier clean-up and flash removal. For example, a layer can be thicker around the periphery of the base to provide for easier flash removal, and/or the layer around the periphery of the base can include a color-changing adhesive. Alternatively, the layer near the middle of the base can include an adhesive that cures readily with less light than would be available at the periphery of the base.

In some embodiment, one or more of the above features can be combined. For example, the combination of an adhesive having increased moisture tolerance can be combined with a patterned adhesive that changes color upon curing to provide a multi-layer adhesive that has a reduced incidence of bond failure upon bonding to a moist surface, with easier clean-up.

Multi-layer adhesives as described herein can be prepared by methods known to one of skill in the art. Suitable methods include, for example, applying, dispensing, or printing the layers of adhesive on an appliance or a substrate. Multiple layers may be applied simultaneously or sequentially.

A useful method for applying multiple layers of adhesive on an orthodontic appliance or a substrate includes, for example, using automated fluid dispensing systems such as those available under the trade designation AUTOMOVE from Asymtek (Carlsbad, Calif.). Such automated fluid dispensing systems are useful for dispensing both patterned and non-patterned layers. Other useful systems include, for example, piston dispensing systems and multiple resolution fluid applicators as described, for example, in U.S. Pat. No. 6,513,897 (Tokie).

Once the multi-layer adhesive has been applied to an orthodontic appliance or a substrate, the appliance or substrate can conveniently be packaged in a container. Exemplary containers are well known in the art and are disclosed, for example, in U.S. Pat. No. 5,172,809 (Jacobs et al.) and U.S. Pat. No. 6,089,861 (Kelly et al.).

Figure 7:
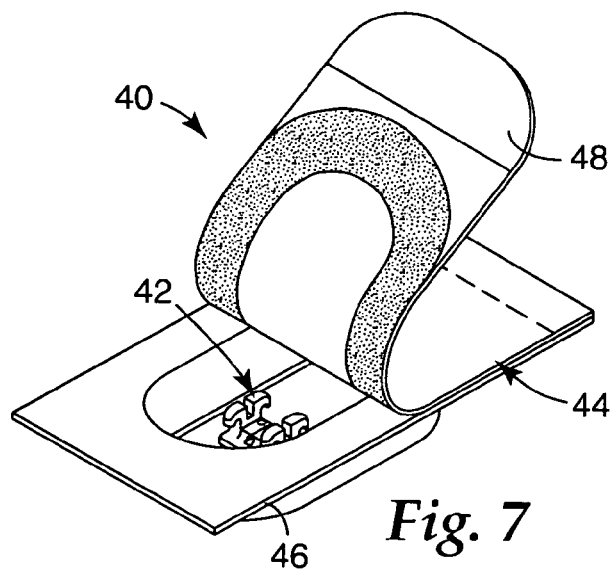
FIG. 7 is a perspective view of a packaged article illustrating an orthodontic appliance having a multi-layer adhesive coated on the base thereof in a container in which the cover has been partially opened.

Referring to FIG. 7, an exemplary embodiment of packaged article 40 including orthodontic appliance 42 having a multi-layer adhesive coated on the base thereof is shown. Package 44 includes container 46 and cover 48. Cover 48, which is releasably connected to container 46 as initially provided, is peeled from container 46 to open the package for removal of orthodontic appliance 42. In FIG. 7, cover 48 has been peeled back from container 46 to partially open package 44.

In preferred embodiments, the package provides excellent protection against degradation of the multi-layer adhesives (e.g., photocurable materials), even after extended periods of time. Such containers are particularly useful for protecting dyes that impart a color changing feature to the multi-layer adhesives. Such containers preferably effectively block the passage of actinic radiation over a broad spectral range, and as a result, the multi-layer adhesive does not prematurely lose color during storage.

In preferred embodiments, the package includes container 46 comprising a polymer and metallic particles. As an example, container 46 may be made of polypropylene that is compounded with aluminum filler or receives an aluminum powder coating as disclosed, for example, in U.S. Pat. Application Publication No. 2003/0196914 A1 (Tzou et al.). The combination of polymer and metallic particles provides a highly effective block to the passage of actinic radiation to color changing dyes, even though such dyes are known to be highly sensitive to light. Such containers also exhibit good vapor barrier properties. As a result, the rheological characteristics of the multi-layer adhesives are less likely to change over extended periods of time. For example, the improved vapor barrier properties of such containers provide substantial protection against degradation of the handling characteristics of multi-layer adhesives so that the adhesives do not prematurely cure or dry or become otherwise unsatisfactory. Suitable covers 48 for such containers can be made of any material that is substantially opaque to the transmission of actinic radiation so that the multi-layer adhesive does not prematurely cure. Examples of suitable materials for cover 48 include laminates of aluminum foil and polymers. For example, the laminate may comprise a layer of polyethyleneterephthalate, adhesive, aluminum foil, adhesive and oriented polypropylene.

In some embodiments, a packaged orthodontic appliance including a multi-layer adhesive thereon may include a release substrate as described, for example, in U.S. Pat. No. 6,183,249 (Brennan et al.).

In other embodiments, a packaged orthodontic appliance including a multi-layer adhesive thereon may not include a release substrate. In one embodiment, the package includes a substrate with at least one recess with an interior surface. The package includes a means for positioning the orthodontic appliance inside the recess such that the adhesive layers do not separate from the appliance upon removal of the appliance from the recess. Preferably, the package further includes a cover for the recess and a means for maintaining the cover in contact with the substrate, wherein the means for positioning the orthodontic appliance includes means suspending the appliance in the recess such that the adhesive layers do not contact the interior surface of the recess. Such packages are disclosed, for example, in U.S. Pat. No. 5,172,809 (Jacobs et al.).

In another embodiment the orthodontic appliance has a base for bonding the appliance to a tooth structure and a body extending from the base and at least two opposed tiewings extending away from the body. The base and at least one of the tiewings extend past the body in a gingival direction and present a gingival recess. The base and at least one other of the tiewings extend past the body in an occlusal direction and present an occlusal recess. The package includes a carrier having a pair of arms extending toward each other. Each of the arms has an outer end section, with the outer end sections being spaced apart from each other and presenting a channel therebetween. The orthodontic appliance is located in the channel and is supported by the arms with one of the outer end sections extending into the occlusal recess and the other of the outer end sections extending into the gingival recess. Such orthodontic appliances and packages are described, for example, in U.S. Pat. No. 6,089,861 (Kelly et al.).

In some embodiments, a packaged article can include a set of orthodontic appliances, wherein at least one of the appliances has a multi-layer adhesive thereon. In some embodiments, some or all of the appliances may have different adhesives or multi-layer adhesives thereon. For example, a packaged article may include both brackets and buccal tubes, and the brackets may each have the same or different adhesive or multi-layer adhesive thereon as the buccal tube. This provides for flexibility for tailoring adhesive properties for the desired end use. For example, more hydrophilic adhesives may be used for posterior appliances, softer adhesives may be used for appliances having larger bonding bases (e.g., posterior appliances), and adhesives capable of developing higher bond strengths may be used for cuspid and bicuspid appliances. Additional examples of articles and sets of appliances are described in applicant's pending U.S. patent application Ser. No. 10/742,561 entitled "PACKAGED ORTHODONTIC ASSEMBLY WITH ADHESIVE PRECOATED APPLIANCES" and filed on even date herewith. Packaged orthodontic appliances are described, for example, in U.S. Pat. Application Publication No. 2003/0196914 A1 (Tzou et al.) and U.S. Pat. No. 4,978,007 (Jacobs et al.), U.S. Pat. No. 5,015,180 (Randklev), U.S. Pat. No. 5,328,363 (Chester et al.), and U.S. Pat. No. 6,183 249 (Brennan et al.).

In direct bonding methods, the orthodontic appliance having a multi-layer adhesive thereon is removed from the package and placed directly on the desired tooth surface and allowed to cure.

In some embodiments of the present invention, an adhesive delivery system is provided that includes a multi-layer adhesive extending across at least a portion of an adhesive transfer area of a substrate. The substrate may optionally be provided as a packaged article. After removing the substrate having the multi-layer adhesive thereon from the package, if present, the multi-layer adhesive may be transferred to the base of an orthodontic appliance, which can then be bonded to a tooth structure either through direct or indirect methods. Exemplary adhesive delivery systems are described, for example, in U.S. Pat. No. 6,213,767 (Dixon et al.).

The multi-layer adhesives disclosed in the present application may also be used for indirect bonding methods. For indirect bonding methods, orthodontic appliances are removed from the package and placed, for example, on a replica plaster or "stone" model of the patient's dental arch to provide a custom base for later mounting on the patient's tooth structure, commonly using a placement device. In one embodiment, the orthodontic appliances have multi-layer adhesives on the bases thereof to bond to the replica plaster or "stone" model, to provide the custom base. Exemplary indirect bonding methods are described, for example, in copending U.S. patent application Ser. No. 10/678,286, filed Oct. 3, 2003.

Figure 8:
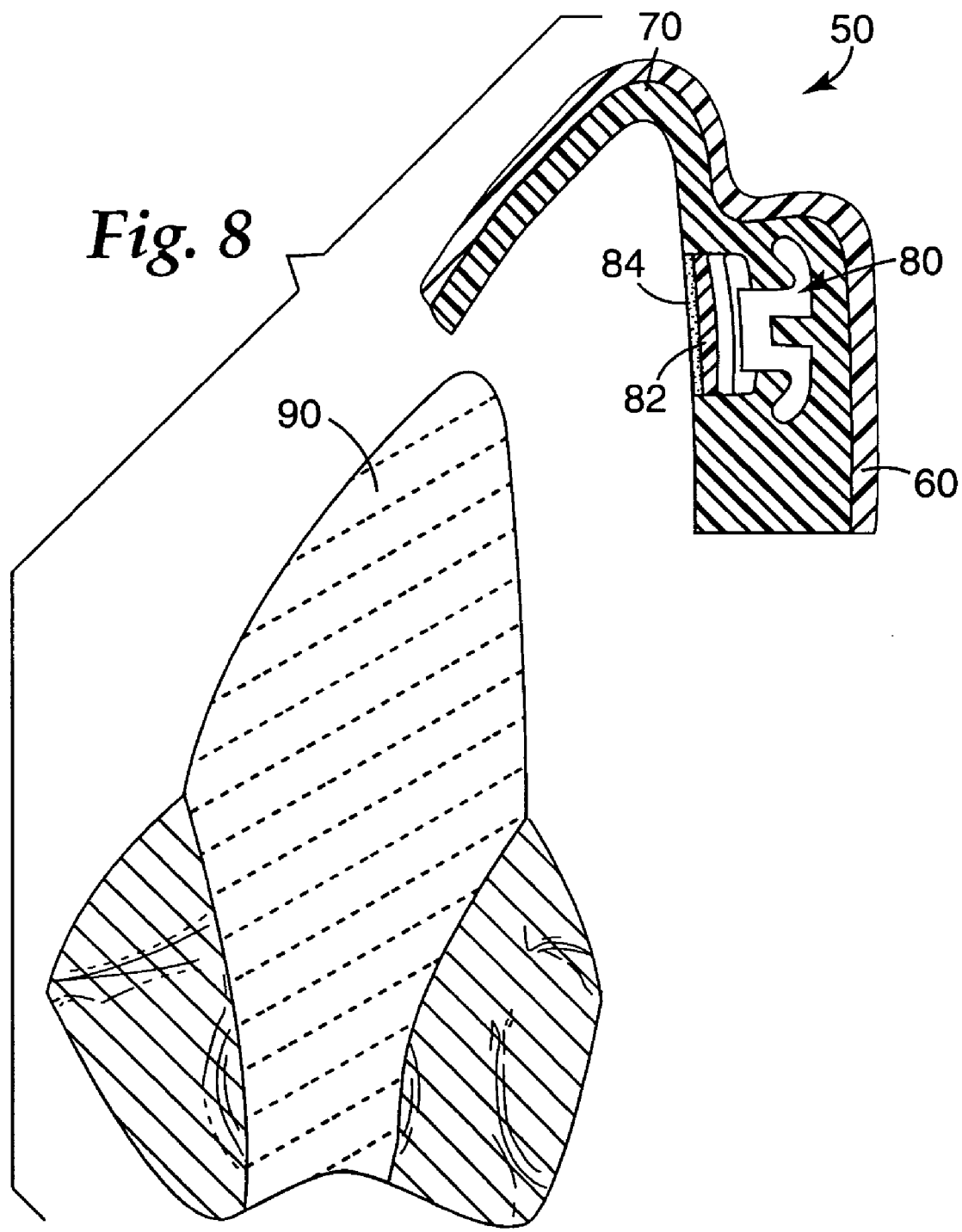
FIG. 8 is an enlarged side cross-sectional view showing the act of applying a dental appliance to a patient's tooth using a placement device used with an indirect bonding method.

In another embodiment of indirect bonding methods, the orthodontic appliance provided in the placement device may have multi-layer adhesives on the custom bases for bonding to the patient's teeth. Referring to FIG. 8, the placement device 50 (comprising shell 60, matrix material 70, and appliances 80) is shown in cross-sectional view. The appliances 80 include custom bases 82 that are coated with multi-layer adhesive 84. The placement device 50 is then placed in a package by the manufacturer and shipped to the practitioner's office.

Once the patient has returned to the office, bonding procedure is undertaken. Preferably, any tooth preparation steps are carried out before the packaged placement device is opened. In this manner, the multi-layer adhesive 84 is not unduly exposed to ambient light or air. After any tooth preparation steps are completed, the package is opened and placement device 50 is removed from the package.

The shell 60 is then positioned over the corresponding teeth and seated, optionally with a swinging, hinge-type motion. In FIG. 8, the patient's tooth is designated by the numeral 90. Since the shape of the cavity of the matrix material 70 matches the shape of the underlying teeth, the appliances 80 are simultaneously seated against the underlying teeth 90 at precisely the same locations corresponding to the previous position of the appliances 80 on the replica. Preferably, pressure is then applied to the occlusal, labial and buccal surfaces of the shell 60 until such time as the multi-layer adhesive 84 has sufficiently hardened. Optionally, finger pressure may be used to firmly press the appliances 80 against the enamel surfaces of the patient's teeth 90.

Once the multi-layer adhesive 84 has hardened, the shell 60 is carefully removed from the patient's dental arch. Preferably, the shell 60 is first separated from the matrix material 70, which remains in place over the dental arch along with the appliances 80. Next, the matrix material 70 is detached from the appliances 80. Optionally, a hand instrument such as a scaler may be used to help hold each appliance 80 against the surface of the respective tooth 90 of the patient as the matrix material 70 is peeled away from the appliances 80. However, in instances where a relatively soft matrix material is employed or otherwise readily releases from the appliances 80, the use of a scaler to help avoid fracturing the fresh adhesive bond is optional. As another option, the shell 60 may be separated from the matrix material 70 before the multi-layer adhesive 84 has hardened. This option is particularly useful when the multi-layer adhesive 84 includes a light-curable adhesive. Once the matrix material 70 has been detached from the appliances 80, an archwire is placed in the slots of the appliances 80 and ligated in place.

EXAMPLES

The following examples are given to illustrate, but not limit, the scope of this invention. Unless otherwise indicated, all parts and percentages are by weight and all molecular weights are weight average molecular weight.

TABLE 1

| Abbreviations, Descriptions, and Sources of Materials | |
|---|---|
| HEMA | 2-Hydroxyethyl methacrylate (CAS No. 868-77-9) |
| Adhesive A | A color-changing, light cure adhesive similar to that described in U.S. Pat. Application Publication No. 2003/0198914 A1 (Brennan et al.), Example 10. |
| Adhesive B | A light cure adhesive similar to that described in PCT International Publication No. WO 00/69393 (Brennan et al.), as listed in Table 2, Sample A. |
| Transbond LR | A light cure adhesive available under the trade designation Transbond LR from 3M Unitek (Monrovia, CA) |
| Transbond MIP | A moisture insensitive primer available under the trade designation Transbond MIP from 3M Unitek (Monrovia, CA) |
| APC II | A light cure adhesive coated appliance available under the trade designation APC II from 3M Unitek (Monrovia, CA) |
| Transbond Plus SEP | A self etching primer available under the trade designation Transbond Plus from 3M Unitek (Monrovia, CA) |
| Transbond XT | A light cure adhesive available under the trade designation Transbond XT from 3M Unitek (Monrovia, CA) |

Bond Strength Test Method

Bond strength was tested by adhering adhesive coated orthodontic brackets to bovine teeth. The brackets used were either ceramic brackets having bases with protruding alumina particles for contact with adhesive, or metal brackets having either mesh or integral molded bases. Brackets commercially available with precoated adhesive were used as received. For brackets without precoated adhesive, the brackets were treated with an adhesive as described herein below. The adhesive samples were applied either by syringe or using an automated fluid dispensing system available under the trade designation AUTOMOVE A-403 from Asymtek (Carlsbad, Calif.).

In some examples, the bovine teeth were first cleaned with a pumice aqueous slurry and rinsed. The teeth were then etched with 37% phosphoric acid etching solution, rinsed with water and dried with moisture-free and oil-free air. The teeth were then treated with a moisture insensitive primer available under the trade designation TRANSBOND MIP from 3M Unitek (Monrovia, Calif.), following the manufacturer's instructions.

Alternately, in other examples, the pumiced teeth were treated with a self etching primer available under the trade designation TRANSBOND Plus SEP from 3M Unitek (Monrovia, Calif.), following the manufacturer's instructions. The brackets with applied adhesive were then seated onto the teeth and pressed firmly to extrude any excess adhesive. The excess was cleaned away.

The adhesive was then cured according to manufacturers instructions using a curing unit available under the trade designation ORTHO Lite from 3M Unitek (Monrovia, Calif.) (e.g., 10 seconds through the bracket for brackets available under the trade designation TRANSCEND from 3M Unitek (Monrovia, Calif.)). The samples of teeth and bonded brackets were stored overnight in 37° C. water.

Bond strength testing was performed by engaging a 0.50-mm round stainless steel wire loop under the occlusal tie wings. Using a universal load frame available from MTS Systems Corporation (Eden Prairie, Minn.), a load was applied in a shear/peel mode until debonding of the bracket from the tooth occurred. The wire attached to the universal load frame was pulled at a rate of 5 mm/minute. The maximum force (in units of pounds) was recorded as bond strength per bracket and reported as results of the "dry" tooth condition test.

In a variation of this test method, moisture (in the form of distilled water by a spray bottle or saliva by a cotton swab) was applied to the etched and/or primed bovine teeth before bonding the adhesive-coated brackets to the teeth. The maximum force was recorded as bond strength per bracket and reported as results of the "wet" tooth condition test.

Color Test

Quantification of initial and bleached color of adhesive samples was performed with a portable ultraviolet-visible (UV-Vis) spectrometer available under the trade designation EPP2000C from StellarNet, Inc. (Oldsmar, Fla.) equipped with a 400-micron fiber reflectance probe and colorimeter software available under the trade designation SpectraWiz CIELAB from StellarNet, Inc. (Oldsmar, Fla.).

To prepare samples for color measurement, an adhesive sample was extruded onto a polyester release liner, a metal ring was placed around the adhesive, and a second release liner was placed on top of the adhesive. The resulting construction was then pressed between two Plexiglas plates with the metal ring controlling the adhesive thickness to 0.51 mm. With the light source of the spectrometer switched off, the adhesive sample between the two release liners was placed on top of a white reflectance standard (Part No. RS50, 50-millimeter diameter, Halon type >97% reflectance, 300-1500 nanometers, StellarNet, Inc.). The fiber optic probe of the spectrometer was positioned 6.3 millimeters above the sample at a 45° angle. Color measurements were taken through the top release liner at an exposure time of 1000 milliseconds and with the center of the adhesive under the beam. The software captured the reflectance spectrum and converted the input to L*, a* and b* values. The a* value was indicative of the redness of the sample with higher numbers indicative of greater redness.

Cured adhesive samples were prepared in the same manner described herein, except that the adhesive pressed between the two polyester release liners was cured for 3 minutes in a light curing oven available under the trade designation TRIAD 2000 from Dentsply International, Inc. (York, Pa.). The cured adhesive sample with the polyester liners intact was placed directly onto the white reflectance standard. The light source of the spectrometer was switched on and L*, a* and b* values were measured as described herein with each reported value representing the average of 3 measurements.

Example 1

Upper lateral brackets available as Unitek Miniature Twin V-slot metal brackets, Cat. No. 017-333 from 3M Unitek (Monrovia, Calif.), were coated with light cure Adhesive B in an amount sufficient to coat the entire base of the bracket when applied to a tooth. The brackets were bonded to etched bovine teeth using the procedure described herein above without the use of either Transbond MIP or Transbond Plus SEP, resulting in a "dry" tooth condition bond strength of 21.7 MPa with a standard deviation of 5.7 MPa (45 pounds per bracket with a standard deviation of 11.8 pounds per bracket) and a "wet" tooth condition bond strength of 9.2 MPa with a standard deviation of 6.6 MPa (19 pounds per bracket with a standard deviation of 13.7 pounds per bracket).

Some of the appliances described in the paragraph herein above were dipped into stabilized HEMA to form multi-layer adhesive coated brackets having a layer of HEMA on the adhesive. The multi-layer adhesive coated brackets were then bonded to bovine teeth using the procedure described herein above without the use of either Transbond MIP brand primer or Transbond Plus SEP brand primer, resulting in a "wet" tooth condition bond strength of 20.3 MPa with a standard deviation of 5.7 MPa (42 pounds per bracket with a standard deviation of 11.8 pounds per bracket).

The "wet" tooth condition bond strength for the multi-layer adhesive coated bracket illustrates that excellent bond strengths can be obtained without separately applying a primer to the tooth. The "wet" tooth condition bond strength for the multi-layer adhesive coated bracket also illustrates that excellent bond strengths can be obtained under "wet" tooth conditions. The example also illustrates that low viscosity layers (e.g., the HEMA layer) and/or hydrophilic layers (e.g., the HEMA layer) in contact with the tooth may improve the wetting of the tooth surface by the adhesive resulting in increased bond strengths.

Example 2

The single layer and multilayered samples were coated using an automated fluid dispensing system available under the trade designation AUTOMOVE A-403 from Asymtek (Carlsbad, Calif.).

Universal bicuspid brackets available under the trade designation TRANSCEND from 3M Unitek (Monrovia, Calif.) were coated with a continuous layer of color-changing, light cure Adhesive A in an amount sufficient to coat the entire base of the bracket when applied to a tooth. The coated brackets were bonded to bovine teeth using the procedure described herein above, resulting in a "dry" tooth condition bond strength of 7.9 MPa with a standard deviation of 2.7 MPa (20.8 pounds per bracket with a standard deviation of 7.2 pounds per bracket).

Some of the universal bicuspid brackets coated with color-changing, light cure Adhesive A as described in the paragraph herein above, were coated with a second continuous layer of adhesive available under the trade designation Transbond LR from 3M Unitek (Monrovia, Calif.) in an amount sufficient to coat the entire base of the bracket when applied to a tooth. The multi-layer brackets were bonded to bovine teeth using the procedure described herein above, resulting in a "dry" tooth condition bond strength of 10.5 MPa with a standard deviation of 2.2 MPa (27.8 pounds per bracket with a standard deviation of 5.9 pounds per bracket).

The example illustrates that low viscosity adhesive (e.g., a Transbond LR layer) in contact with a tooth may improve the wetting of the tooth surface by the adhesive, resulting in increased bond strengths.

Example 3

The samples were coated using an automated fluid dispensing system available under the trade designation AUTOMOVE A-403 from Asymtek (Carlsbad, Calif.).

Universal bicuspid brackets available under the trade designation TRANSCEND from 3M Unitek (Monrovia, Calif.) were coated with a continuous layer of color-changing, light cure Adhesive A in an amount sufficient to coat the entire base of the bracket when applied to a tooth. The coated brackets were bonded to bovine teeth using the procedure described herein above, resulting in a "dry" tooth condition bond strength of 7.9 MPa with a standard deviation of 2.7 MPa (20.8 pounds per bracket with a standard deviation of 7.2 pounds per bracket).

Universal bicuspid brackets were coated with a continuous layer of a precoat bracket adhesive available under the trade designation of APC II from 3M Unitek (Monrovia, Calif.) in an amount sufficient to coat the entire base of the bracket when applied to a tooth. The brackets were then coated with a second continuous layer of color-changing, light cure Adhesive A in an amount sufficient to coat the entire base of the bracket when applied to a tooth. The multi-layer brackets were bonded to bovine teeth using the procedure described herein above, resulting in a "dry" tooth condition bond strength of 12.0 MPa with a standard deviation of 3.6 MPa (31.6 pounds per bracket with a standard deviation of 9.5 pounds per bracket).

The example illustrates that hydrophobic (APC II) and hydrophilic color-changing, light cure Adhesive A can be placed on the same bracket, resulting in increased bond strengths.

Example 4

The samples were coated using an automated fluid dispensing system available under the trade designation AUTOMOVE A-403 from Asymtek (Carlsbad, Calif.).

Universal bicuspid brackets available under the trade designation TRANSCEND from 3M Unitek (Monrovia, Calif.) were coated with a ribbon of color-changing, light cure Adhesive A around the periphery of the base to form a "donut" shape. A second adhesive available under the trade designation APC II form 3M Unitek (Monrovia, Calif.) was applied onto the center of the "donut" of color-changing, light cure Adhesive A.

The example illustrates that a color-changing "donut" layer that is rich in color promotes easy flash clean-up without the need for dye dispersed throughout all the adhesive(s).

Example 5

Example 4 is repeated except that the color-changing adhesive is also fluoride-releasing.

The example illustrates that a fluoride rich fluoride-releasing "donut" layer at the bonding surface can offer enhanced fluoride release where desired for caries prevention without the need for fluoride release throughout all the adhesive(s).

Example 6

Color-changing, light cure Adhesive A was applied by syringe to upper central brackets available under the trade designation VICTORY SERIES (Cat. No. 017-401 or equivalent) from 3M Unitek (Monrovia, Calif.) in an amount sufficient to coat the entire base of the bracket when applied to a tooth. The adhesive coated brackets were bonded to bovine teeth using the procedure described herein above, resulting in a "wet" tooth condition bond strength of 17.2 MPa with a standard deviation of 7.3 MPa (42.2 pounds per bracket with a standard deviation of 17.8 pounds per bracket).

Using some of the color-changing adhesive coated brackets described in the paragraph herein above, Transbond MIP adhesive was brushed on the color-changing adhesive and then air dried using filtered, dry compressed air to form multi-layer adhesive coated brackets having a layer of Transbond MIP on the precoated color-changing adhesive. The adhesive layers were dried using filtered, dry compressed air. The multi-layer adhesive coated brackets were bonded to bovine teeth using the procedure described herein above, except that no primer was added to the tooth prior to bonding, resulting in a "wet" tooth condition bond strength of 17.9 MPa with a standard deviation of 6.5 MPa (43.9 pounds per bracket with a standard deviation of 16 pounds per bracket).

The "wet" tooth condition bond strength for the multi-layer adhesive coated bracket illustrates that excellent bond strengths can be obtained under "wet" tooth conditions. The "wet" tooth condition bond strength for the multi-layer adhesive coated bracket also illustrates that excellent bond strengths can be obtained without separately applying a primer to the tooth. As such, the number of steps required in the typical orthodontic bonding process may be reduced by eliminating the priming step.

Example 7

This example illustrates that a continuous layer of self etching primer in a multi-layer adhesive allows elimination of both the etching and priming steps.

A continuous layer of mono- and di-HEMA phosphates, as described, for example, in copending U.S. Provisional Patent Application Ser. No. 60/494,603, filed Aug. 12, 2003, was applied over a continuous layer of Transbond XT adhesive in an amount sufficient to coat the entire base of the bracket when applied to a tooth. The coated brackets were pressed onto pumiced, unetched, wet bovine teeth and allowed to sit for 60 seconds. The flash was then cleaned and the adhesive cured with a 3-second exposure mesial and distal with a curing unit available under the trade designation ORTHO Lite from 3M Unitek (Monrovia, Calif.). This resulted in a "wet" tooth condition bond strength of 9.5 MPa with a standard deviation of 2.6 MPa.

The "wet" tooth condition bond strength for the multi-layer adhesive coated bracket illustrates that excellent bond strengths can be obtained without separately applying a primer to the tooth. As such, the number of steps required in the typical orthodontic bonding process may be reduced by eliminating the priming and etching steps.

Example 8

The property enhancements described herein are not limited to light curing precoat systems. For example, multi-layer chemical cure precoat systems can provide similar benefits over known chemical cure precoat systems.

A two part chemical cure adhesive is produced by dispensing alternating dots of the "A" side and the "B" side on a base of an orthodontic appliance as illustrated in FIG. 6. Separating the two components 34 and 36 ensures that they will not cure before application to the tooth. Pressing the adhesive coated bonding base onto a tooth effectively mixes the two components and allows them to cure. This example shows that a chemical cure adhesive system can be delivered to the doctor in precoated form without requiring the doctor to pretreat the teeth, other than cleaning and etching.

Example 9

This example illustrates the preparation of an orthodontic adhesive delivery system that includes a multi-layer (e.g., a three-layer) adhesive. The orthodontic adhesive delivery system is prepared by dispensing first a thin, low viscosity primer layer onto an adhesive transfer area of a substrate (e.g., a release liner). The first layer includes a hydrophilic resin to provide moisture tolerance, and a fluoride-releasing agent to provide fluoride release. A second, thicker layer is applied on top of the first layer. The second has a higher viscosity and higher filler loading than the first layer. The second layer also includes an effective concentration of a color changing dye. It also includes a fluoride-releasing agent capable of releasing fluoride. A third, thin, adhesion promoting layer is applied. The third layer includes adhesion promoting agents to enhance adhesion to stainless steel metal brackets. This third layer is also lower viscosity than the second layer. The 3-layer adhesive may then be applied to the base of a bracket for bonding to a pumiced, etched tooth by positioning the bracket over the 3-layer adhesive, pushing down slightly to cause the adhesive layers to flow onto the base of the bracket, and lifting up to release the adhesive coated bracket from the adhesive transfer area of the substrate.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A packaged article comprising:
   an orthodontic appliance having a base for bonding the appliance to a tooth structure;
   a first hardenable adhesive layer and a second hardenable adhesive layer, each extending across at least a portion of the base of the appliance, wherein at least one of the first or second layers is a patterned layer, and wherein the first and second layers differ by one or more properties selected from the group consisting of chemical composition, viscosity, hydrophilicity, thickness, curing times, curing mechanisms, color, change in color upon curing, enzyme release, fluoride release, bond strengths upon curing, filler loading, filler types, and pH, and with the proviso that the first and second layers are not in contact with a release substrate; and
   a container at least partially surrounding the orthodontic appliance having the first and second layers thereon.

2. The packaged article of claim 1 wherein the base of the appliance is selected from the group consisting of a base flange, a cured single layer adhesive, a cured multi-layer adhesive, and combinations thereof.

3. The packaged article of claim 1 wherein at least one of the first or second layers is a non-patterned layer.

4. The packaged article of claim 1 wherein at least one of the first or second layers is selected from the group consisting of primer layers, etchant layers, colored layers, color-changing layers, enzyme releasing layers, fluoride releasing layers, adhesion promoting layers, and combinations thereof.

5. The packaged article of claim 1 wherein at least one of the first or second layers comprises a component selected from the group consisting of fluoride releasing agents, adhesive enhancing agents, fillers, micro fillers, enzyme releasing agents, rheology enhancing agents, photobleachable dyes, and combinations thereof.

6. The packaged article of claim 1 wherein at least one of the first or second layers is hardenable by actinic radiation.

7. The packaged article of claim 6 wherein at least one of the first or second layers has an initial color prior to exposure to actinic radiation and a final color that is different from the initial color subsequent to the layer being exposed to actinic radiation.

8. A packaged article comprising:
   an orthodontic appliance having a base for bonding the appliance to a tooth structure;
   a first hardenable adhesive layer and a second hardenable adhesive layer, each extending across at least a portion of the base of the appliance, with the proviso that the first and second layers are not in contact with a release substrate;
   one or more additional hardenable adhesive layers extending across at least a portion of the first or second layers; and
   a container at least partially surrounding the orthodontic appliance having the first, second, and one or more additional layers thereon.

9. The packaged article of claim 8 wherein at least one of the one or more additional layers are in contact with a release substrate.

10. A packaged article comprising:
   a) a substrate with at least one recess with an interior surface,
   b) an orthodontic appliance having a base for bonding the appliance to a tooth structure and having a first hardenable adhesive layer and a second hardenable adhesive layer, each extending across at least a portion of the base of the appliance, with the proviso that neither the first hardenable adhesive layer nor the second hardenable adhesive layer is hardened, and wherein the first and second layers differ by one or more properties selected from the group consisting of chemical composition, viscosity, hydrophilicity, thickness, curing times, curing mechanisms, color, change in color upon curing, enzyme release, fluoride release, bond strengths upon curing, filler loading, filler types, and pH; and
   c) means for positioning the orthodontic appliance inside the recess such that the adhesive layers do not separate from the appliance upon removal of the appliance from the recess;
   d) a cover for the recess; and
   e) means for maintaining the cover in contact with the substrate, wherein the means for positioning the orthodontic appliance includes means suspending the appliance in the recess such that the adhesive layers do not contact the interior surface of the recess.

11. A packaged article comprising:
   an orthodontic appliance having a base for bonding the appliance to a tooth structure, a body extending from the base and at least two opposed tiewings extending away from the body, the base and at least one of the tiewings extending past the body in a gingival direction and presenting a gingival recess, the base and at least one other of the tiewings extending past the body in an occlusal direction and presenting an occlusal recess, wherein the appliance has a first hardenable adhesive layer and a second hardenable adhesive layer, each extending across at least a portion of the base of the appliance, with the proviso that neither the first hardenable adhesive layer nor the second hardenable adhesive layer is hardened, and wherein the first and second layers differ by one or more properties selected from the group consisting of chemical composition, viscosity, hydrophilicity, thickness, curing times, curing mechanisms, color, change in color upon curing, enzyme release, fluoride release, bond strengths upon curing, filler loading, filler types, and pH; and a carrier having a pair of arms extending toward each other, each of the arms having an outer end section, the outer end sections being spaced apart from each other and presenting a channel therebetween, the orthodontic appliance being located in the channel and being supported by the arms with one of the outer end sections extending into the occlusal recess and the other of the outer end sections extending into the gingival recess.

12. An article comprising:
an orthodontic appliance having a base for bonding the appliance to a tooth structure; and
a first hardenable adhesive layer and a second hardenable adhesive layer, each extending across at least a portion of the base of the appliance, with the proviso that neither the first hardenable adhesive layer nor the second hardenable adhesive layer is hardened,
wherein the first and second layers differ by one or more properties selected from the group consisting of chemical composition, viscosity, hydrophilicity, thickness, curing times, curing mechanisms, color, change in color upon curing, enzyme release, fluoride release, bond strengths upon curing, filler loading, filler types, and pH, and
wherein at least one of the first or second adhesive layers comprises a photobleachable dye, and wherein the at least one adhesive has an initial color prior to exposure to actinic radiation and a final color subsequent to exposure to actinic radiation, the initial color being different than the final color.

13. The article of claim 12 wherein the base of the appliance is selected from the group consisting of a base flange, a cured single layer adhesive, a cured multi-layer adhesive, and combinations thereof.

14. The article of claim 12 wherein at least one of the first or second layers is a patterned layer.

15. The article of claim 12 wherein at least one of the first or second layers is a non-patterned layer.

16. The article of claim 12 wherein at least one of the first or second layers is selected from the group consisting of primer layers, etchant layers, colored layers, color-changing layers, enzyme releasing layers, fluoride releasing layers, adhesion promoting layers, and combinations thereof.

17. The article of claim 12 wherein at least one of the first or second layers comprises a component selected from the group consisting of fluoride releasing agents, adhesive enhancing agents, fillers, micro fillers, enzyme releasing agents, rheology enhancing agents, photobleachable dyes, and combinations thereof.

18. The article of claim 12 wherein at least one of the first or second layers is hardenable by actinic radiation.

19. The article of claim 12 wherein at least one of the first or second layers further comprises a hardener comprising a sensitizing compound different from the photobleachable dye.

20. The article of claim 12 wherein the change in color from the initial color to the final color has a $\Delta E^*$ of greater than 10.

21. The article of claim 12 wherein the change in color from the initial color to the final color has a $\Delta E^*$ of greater than 15.

22. The article of claim 12 wherein the change in color from the initial color to the final color has a $\Delta E^*$ of greater than 20.

23. A method of bonding an orthodontic appliance to a tooth structure comprising:
providing an article according to claim 12;
applying the base of the appliance to the tooth structure; and
exposing the adhesive to actinic radiation.

24. An article comprising:
an orthodontic appliance having a base for bonding the appliance to a tooth structure;
a first hardenable adhesive layer and a second hardenable adhesive layer, each extending across at least a portion of the base of the appliance, with the proviso that neither the first hardenable adhesive layer nor the second hardenable adhesive layer is hardened; and
one or more additional hardenable adhesive layers extending across at least a portion of the first or second layers,
wherein at least one of the first or second adhesive layers comprises a photobleachable dye, and wherein the at least one adhesive has an initial color prior to exposure to actinic radiation and a final color subsequent to exposure to actinic radiation, the initial color being different than the final color.

25. An article comprising:
an orthodontic appliance having a base for bonding the appliance to a tooth structure;
a first hardenable adhesive layer extending across at least a portion of the base of the appliance and covering a first area; and
a second hardenable adhesive layer extending across at least a portion of the base of the appliance and covering a second area,
wherein the second area is different than the first area,
wherein the first and second layers differ by one or more properties selected from the group consisting of chemical composition, viscosity, hydrophilicity, thickness, curing times, curing mechanisms, color, change in color upon curing, enzyme release, fluoride release, bond strengths upon curing, filler loading, filler types, and pH, and
wherein at least one of the first or second layers is a patterned layer.

26. The article of claim 25 wherein the first area is coextensive with the base of the appliance.

27. The article of claim 26 wherein the second area is smaller than the first area.

28. The article of claim 27 wherein the second area is proximate the center of the base of the appliance.

29. The article of claim 25 further comprising:
one or more additional hardenable adhesive layers extending across at least a portion of the first or second layers.

30. The article of claim 25 wherein at least one of the first or second layers is a non-patterned layer.

31. The article of claim 25 wherein at least one of the first or second layers is selected from the group consisting of primer layers, etchant layers, colored layers, color-changing layers, enzyme releasing layers, fluoride releasing layers, adhesion promoting layers, and combinations thereof.

32. The article of claim 25 wherein at least one of the first or second layers comprises a component selected from the group consisting of fluoride releasing agents, adhesive enhancing agents, fillers, micro fillers, enzyme releasing agents, rheology enhancing agents, photobleachable dyes, and combinations thereof.

33. The article of claim 25 wherein at least one of the first or second layers is hardenable by actinic radiation.

34. The article of claim 33 wherein at least one of the first or second layers has an initial color prior to exposure to actinic radiation and a final color that is different from the initial color subsequent to the layer being exposed to actinic radiation.

35. A method of bonding an orthodontic appliance to a tooth structure comprising:
  providing an article according to claim 25;
  applying the base of the appliance to the tooth structure; and
  exposing the adhesive to actinic radiation.

36. A method of preparing a precoated orthodontic appliance comprising:
  providing an orthodontic appliance having a base for bonding the appliance to a tooth structure;
  disposing a first hardenable adhesive layer on at least a portion of the base of the appliance; and
  disposing a second hardenable adhesive layer on at least a portion of the base of the appliance, with the proviso that neither the first hardenable adhesive layer nor the second hardenable adhesive layer is hardened,
  wherein the first and second layers differ by one or more properties selected from the group consisting of chemical composition, viscosity, hydrophilicity, thickness, curing times, curing mechanisms, color, change in color upon curing, enzyme release, fluoride release, bond strengths upon curing, filter loading, filler types, and pH, and
  wherein at least one of the first or second layers is a patterned layer.

37. The method of claim 36 wherein disposing at least one of the adhesive layers comprises printing or dispensing the at least one layer.

38. A method of preparing a precoated orthodontic appliance comprising:
  providing an orthodontic appliance having a base for bonding the appliance to a tooth structure;
  disposing a first hardenable adhesive layer on at least a portion of the base of the appliance;
  disposing a second hardenable adhesive layer on at least a portion of the base of the appliance; and
  applying a release substrate on at least one of the adhesive layers,
  wherein the first and second layers differ by one or more properties selected from the group consisting of chemical composition, viscosity, hydrophilicity, thickness, curing times, curing mechanisms, color, change in color upon curing, enzyme release, fluoride release, bond strengths upon curing, filler loading, filler types, and pH.

* * * * *

UNITED STATES PATENT AND TRADEMARK OFFICE
CERTIFICATE OF CORRECTION

PATENT NO. : 7,374,420 B2  Page 1 of 1
APPLICATION NO. : 10/740980
DATED : May 20, 2008
INVENTOR(S) : Joan V. Brennan It is certified that error appears in the above-identified patent and that said Letters Patent is hereby corrected as shown below:

Title Pg, Item (75)
Inventors, delete "David K. Cinader" and insert -- David K. Cinader, Jr. --, therefore.

Column 22
Line 3, In Claim 36, delete "filter" and insert -- filler --, therefore.

Signed and Sealed this

Sixteenth Day of December, 2008

JON W. DUDAS
*Director of the United States Patent and Trademark Office*